(12) United States Patent
Fukuda

(10) Patent No.: US 10,950,013 B2
(45) Date of Patent: Mar. 16, 2021

(54) IMAGE PROCESSING APPARATUS, IMAGE PROCESSING METHOD, AND IMAGE PROCESSING PROGRAM

(71) Applicant: FUJIFILM Corporation, Tokyo (JP)

(72) Inventor: Wataru Fukuda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 149 days.

(21) Appl. No.: 16/204,317

(22) Filed: Nov. 29, 2018

(65) Prior Publication Data
US 2019/0221012 A1 Jul. 18, 2019

(30) Foreign Application Priority Data

Jan. 17, 2018 (JP) .............................. JP2018-005702

(51) Int. Cl.
| G06T 11/00 | (2006.01) |
| A61B 6/03 | (2006.01) |
| A61B 6/00 | (2006.01) |
| A61B 6/02 | (2006.01) |

(52) U.S. Cl.
CPC ............ *G06T 11/008* (2013.01); *A61B 6/025* (2013.01); *A61B 6/032* (2013.01); *A61B 6/4452* (2013.01); *A61B 6/5205* (2013.01); *A61B 6/5223* (2013.01); *A61B 6/542* (2013.01); *A61B 6/545* (2013.01); *G06T 11/006* (2013.01); *A61B 6/4417* (2013.01); *A61B 6/488* (2013.01);
(Continued)

(58) Field of Classification Search
CPC ..... G06T 11/006; G06T 11/008; A61B 6/025; A61B 6/032; A61B 6/488; A61B 6/542; A61B 6/545; A61B 6/5205; A61B 6/5223; A61B 6/5235; A61B 6/5258; A61B 6/4417; A61B 6/4452
USPC ........................................................ 382/131
See application file for complete search history.

(56) References Cited

U.S. PATENT DOCUMENTS

| 8,373,652 B2* | 2/2013 | Masuzawa ............ G06T 11/008 345/156 |
| 2007/0183564 A1* | 8/2007 | Li .......................... A61B 6/465 378/22 |
| 2013/0198687 A1 | 8/2013 | Bird et al. |

(Continued)

FOREIGN PATENT DOCUMENTS

| JP | 2008-154647 A | 7/2006 |
| JP | 2013-154162 A | 8/2013 |

(Continued)

OTHER PUBLICATIONS

Japanese Office Action for corresponding Japanese Application No. 2018-005702, dated Jan. 5, 2021, with English translation.

*Primary Examiner* — Daniel G Mariam
(74) *Attorney, Agent, or Firm* — Birch, Stewart, Kolasch & Birch, LLP

(57) ABSTRACT

In a console, a control unit functions as an acquisition unit and a generation unit according to the present disclosure. The acquisition unit acquires a plurality of projection images obtained by irradiating a subject disposed between a radiation source and a radiation detector with radiation emitted from the radiation source at different irradiation angles and capturing the radiation with the radiation detector at each of the irradiation angles. The generation unit generates a slab image with a thickness corresponding to the range from a first height to a second height.

20 Claims, 10 Drawing Sheets

(52) U.S. Cl.
CPC ........... *A61B 6/5235* (2013.01); *A61B 6/5258* (2013.01); *G06T 2207/10081* (2013.01)

(56) References Cited

U.S. PATENT DOCUMENTS

| | | | |
|---|---|---|---|
| 2016/0367210 A1 | 12/2016 | Gkanatsios et al. | |
| 2017/0084059 A1 | 3/2017 | Hagiwara | |
| 2017/0231593 A1 | 8/2017 | Fukuda et al. | |
| 2017/0281110 A1* | 10/2017 | Mandelkern | A61B 6/5205 |
| 2019/0043456 A1 | 2/2019 | Kreeger et al. | |

FOREIGN PATENT DOCUMENTS

| | | |
|---|---|---|
| JP | 2014-534042 A | 12/2014 |
| JP | 2015-159961 A | 9/2015 |
| JP | 2017-510323 A | 4/2017 |
| JP | 2017-143943 A | 8/2017 |
| WO | WO 2016/099924 A1 | 6/2016 |

* cited by examiner

IMAGE PROCESSING APPARATUS, IMAGE PROCESSING METHOD, AND IMAGE PROCESSING PROGRAM

CROSS-REFERENCE TO RELATED APPLICATIONS

The present application claims priority under 35 U.S.C. § 119 to Japanese Patent Application No. 2018-005702, filed on Jan. 17, 2018. Each of the above application is hereby expressly incorporated by reference, in its entirety, into the present application.

BACKGROUND OF THE INVENTION

1. Field of the Invention

The present disclosure relates to an image processing apparatus, a non-transitory recording medium storing an image processing method, and an image processing program.

2. Description of the Related Art

As a radiography method, so-called tomosynthesis imaging has been known which sequentially emits radiation from each of a plurality of irradiation positions with different irradiation angles and captures a plurality of projection images at each irradiation position using a radiation detector. In addition, a technique has been known which generates a tomographic image from a plurality of projection images obtained by tomosynthesis imaging, using a reconstruction process.

Further, a technique has been known which generates a plurality of tomographic images with different heights from a detection surface of a radiation detector and combines the plurality of generated tomographic image to generate a slab image having so-called information corresponding to a thickness including information related to a certain range in a height direction (see WO2016/099924A and JP2015-159961A). The technique disclosed in WO2016/099924A and JP2015-159961A can generate 10 tomographic images at an interval of, for example, 1 mm in the height direction and combine the 10 generated tomographic images to generate a slab image with a thickness of 1 mm.

SUMMARY OF THE INVENTION

In the technique disclosed in WO2016/099924A and JP2015-159961A, first, it is necessary to generate a plurality of tomographic images in order to generate the slab image. Therefore, the technique has the problem that an arithmetic processing load required for generation is relatively large.

The present disclosure has been made in view of the above-mentioned problem and an object of the present disclosure is to provide an image processing apparatus, an image processing method, and an image processing program that can reduce an arithmetic processing load required to generate a slab image.

In order to achieve the object, according to a first aspect of the present disclosure, there is a provided an image processing apparatus comprising: an acquisition unit that acquires a plurality of projection images obtained by irradiating a subject disposed between a radiation source and a radiation detector with radiation emitted from the radiation source at different irradiation angles and capturing the radiation with the radiation detector at each of the irradiation angles; and a generation unit that generates a slab image with a thickness corresponding to a range from a first height to a second height different from the first height, using a value of a first pixel in each of the plurality of projection images corresponding to coordinates of a pixel of interest in a tomographic plane whose height from a detection surface of the radiation detector is the first height and a value of a second pixel in each of the plurality of projection images corresponding to the coordinates of the pixel of interest in a tomographic plane at the second height.

According to a second aspect of the present disclosure, in the image processing apparatus according to the first aspect, the generation unit may generate the slab image further using a value of a third pixel in each of the plurality of projection images corresponding to the coordinates of the pixel of interest in a tomographic plane at a third height of at least a position between the first height and the second height.

According to a third aspect of the present disclosure, in the image processing apparatus according to the second aspect, the generation unit may generate the slab image using at least one of a mean, a minimum value, a maximum value, or a mode of the value of the first pixel in each of the plurality of projection images, the value of the second pixel in each of the plurality of projection images, and the value of the third pixel in each of the plurality of projection images.

According to a fourth aspect of the present disclosure, in the image processing apparatus according to the first aspect, the generation unit may generate the slab image using values of pixels located from the first pixel to the second pixel in each of the plurality of projection images.

According to a fifth aspect of the present disclosure, in the image processing apparatus according to the fourth aspect, the generation unit may generate the slab image using at least one of a mean, a minimum value, a maximum value, or a mode of the values of the pixels located from the first pixel to the second pixel in each of the plurality of projection images.

According to a sixth aspect of the present disclosure, in the image processing apparatus according to the third or fifth aspect, the generation unit may determine which of the mean, the minimum value, the maximum value, and the mode to use, on the basis of a size of an object of interest in the subject.

According to a seventh aspect of the present disclosure, in the image processing apparatus according to any one of the first to sixth aspects, the first height may be a height of a lowermost portion in the height direction and the second height may be a height of an uppermost portion in the height direction.

According to an eighth aspect of the present disclosure, in the image processing apparatus according to any one of the first to sixth aspects, the generation unit may generate a plurality of the slab images while changing the first height and the second height in the height direction and combine the plurality of generated slab images to further generate a two-dimensional corresponding image.

According to a ninth aspect of the present disclosure, in the image processing apparatus according to any one of the first to eighth aspects, the generation unit may decompose each of the plurality of projection images into a plurality of frequency images indicating spatial frequencies in different bands, perform different types of image processing for the plurality of frequency images, combine the plurality of frequency images to generate a plurality of projection images, and generate the slab image on the basis of the plurality of combined projection images.

In order to achieve the object, according to a tenth aspect of the present disclosure, there is provided an image processing method comprising: acquiring a plurality of projection images obtained by irradiating a subject disposed between a radiation source and a radiation detector with radiation emitted from the radiation source at different irradiation angles and capturing the radiation with the radiation detector at each of the irradiation angles; and generating a slab image with a thickness corresponding to a range from a first height to a second height different from the first height, using a value of a first pixel in each of the plurality of projection images corresponding to coordinates of a pixel of interest in a tomographic plane whose height from a detection surface of the radiation detector is the first height and a value of a second pixel in each of the plurality of projection images corresponding to the coordinates of the pixel of interest in a tomographic plane at the second height.

In order to achieve the object, according to an eleventh aspect of the present disclosure, there is provided a non-transitory recording medium storing an image processing program that causes a computer to perform: acquiring a plurality of projection images obtained by irradiating a subject disposed between a radiation source and a radiation detector with radiation emitted from the radiation source at different irradiation angles and capturing the radiation with the radiation detector at each of the irradiation angles; and generating a slab image with a thickness corresponding to a range from a first height to a second height different from the first height, using a value of a first pixel in each of the plurality of projection images corresponding to coordinates of a pixel of interest in a tomographic plane whose height from a detection surface of the radiation detector is the first height and a value of a second pixel in each of the plurality of projection images corresponding to the coordinates of the pixel of interest in a tomographic plane at the second height.

According to the present disclosure, it is possible to reduce an arithmetic processing load required to generate a slab image.

DESCRIPTION OF THE PREFERRED EMBODIMENTS

Hereinafter, embodiments of the invention will be described in detail with reference to the drawings. These embodiments do not limit the invention.

First Embodiment

Figure 1:
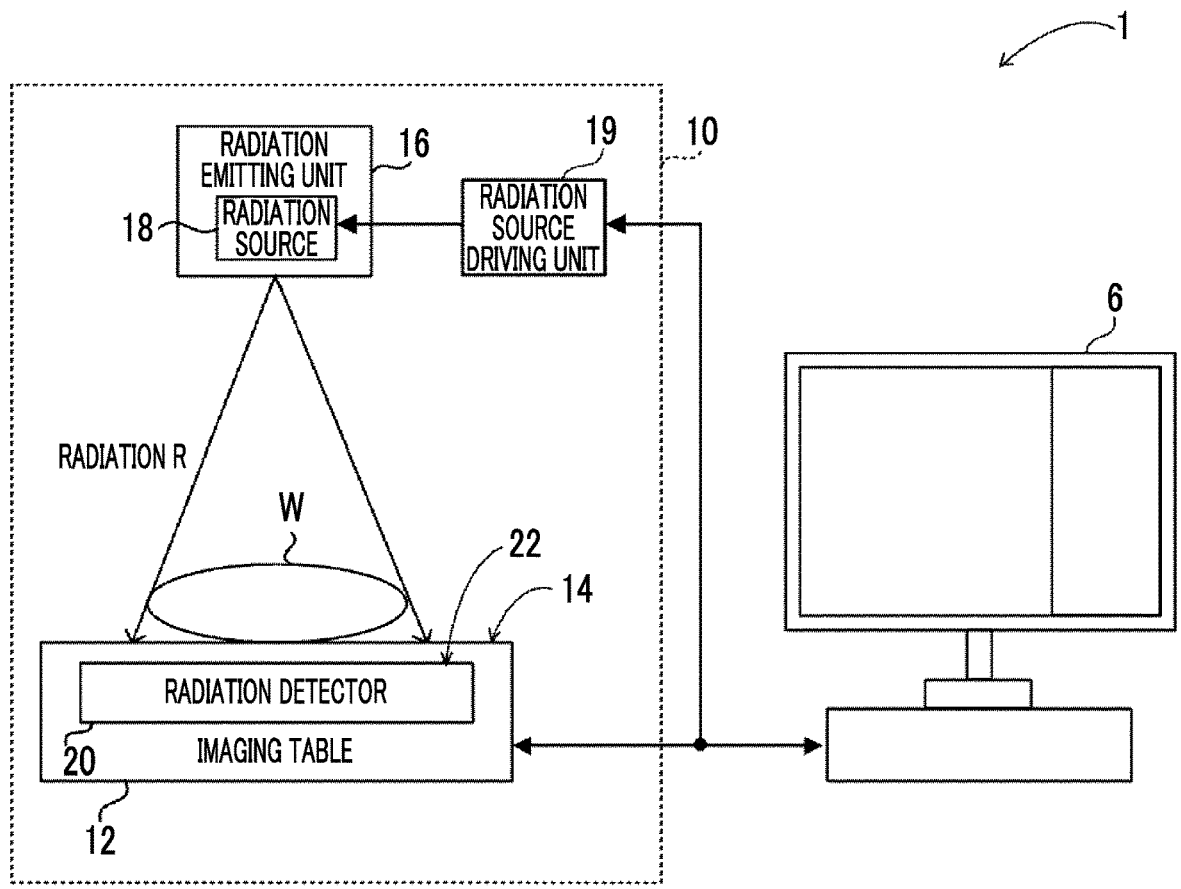
FIG. 1 is a diagram illustrating an example of the overall configuration of a radiography system according to a first embodiment.
Figure 2:
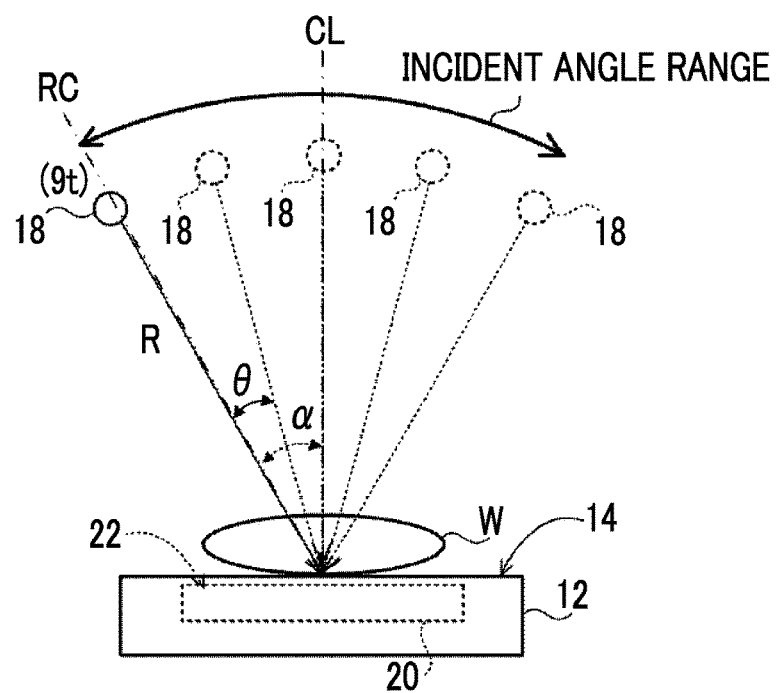
FIG. 2 is a diagram illustrating tomosynthesis imaging performed by a radiography apparatus according to the first embodiment.

First, an example of the overall configuration of a radiography system according to this embodiment will be described. FIG. 1 is a diagram illustrating an example of the overall configuration of a radiography system 1 according to this embodiment. In addition, FIG. 2 is a diagram illustrating tomosynthesis imaging (which will be described in detail below) by a radiography apparatus 10 according to this embodiment.

As illustrated in FIG. 1, the radiography system 1 according to this embodiment comprises a console 6 and the radiography apparatus 10. In the radiography system 1 according to this embodiment, the radiography apparatus 10 captures a radiographic image of a subject W on the basis of a command (imaging order) input from an external system (for example, a radiology information system (RIS)) through the console 6 in response to the operation of a user such as a doctor or a radiology technician.

Figure 3:
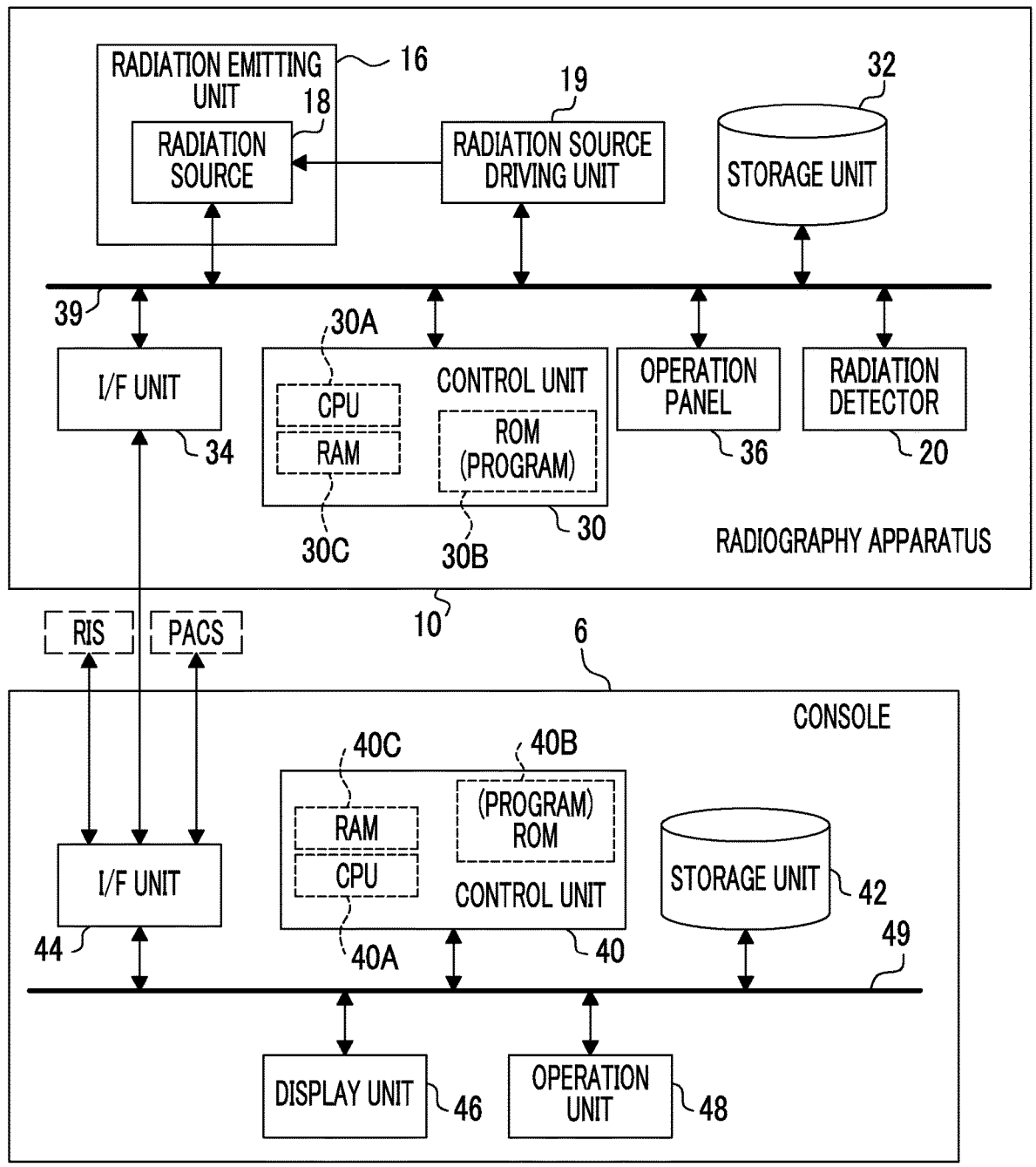
FIG. 3 is a block diagram illustrating an example of the configuration of a console and the radiography apparatus according to the first embodiment.

FIG. 3 is a block diagram illustrating an example of the configuration of the console 6 and the radiography apparatus 10 according to this embodiment. Hereinafter, the console 6 and the radiography apparatus 10 according to this embodiment will be described with reference to FIGS. 1 to 3. The console 6 according to this embodiment is an example of an image processing apparatus according to the present disclosure.

The radiography apparatus 10 according to this embodiment is an apparatus that irradiates the subject W with radiation R (for example, X-rays) and captures the radiographic image of the subject W. In addition, the radiography apparatus 10 according to this embodiment has a function of performing so-called tomosynthesis imaging (which will be described in detail below) and simple imaging.

A radiation detector 20 that detects the radiation R transmitted through the subject W and an imaging surface 14 of an imaging table 12 is provided in the imaging table 12. The radiography apparatus 10 generates a radiographic image on the basis of the radiation R detected by the radiation detector 20. However, the type of radiation detector 20 is not particularly limited. For example, the radiation detector 20 may be an indirect-conversion-type radiation detector that converts the radiation R into light and converts the converted light into charge or a direct-conversion-type radiation detector that directly converts the radiation R into charge. In this embodiment, image data indicating the radiographic image output from the radiation detector 20 of the radiography apparatus 10 is transmitted to the console 6.

A radiation source 18 provided in a radiation emitting unit 16 of the radiography apparatus 10 is supported while being separated from the imaging surface 14 of the imaging table 12, that is, a detection surface 22 of the radiation detector 20 by a predetermined distance.

In a case in which the radiography apparatus 10 performs the tomosynthesis imaging, a radiation source driving unit 19 continuously moves the radiation source 18 of the radiation emitting unit 16 to each of a plurality of irradiation positions with different irradiation angles (projection angles). In this embodiment, as illustrated in FIG. 2, the radiation source 18 is moved to irradiation positions $9t$ (t=0, 1, ..., T; in FIG. 2, T=5) with different irradiation angles which are spaced a predetermined angle $\theta$ apart, that is, the positions where the incident angles of the radiation R with respect to the detection surface 22 of the radiation detector 20 are different from each other. At each irradiation position, the radiation source 18 emits the radiation R in response to a command from the console 6 and the radiation detector 20 captures a radiographic image. Hereinafter, in the tomosynthesis imaging, the radiographic images captured by the radiation detector 20 at a plurality of irradiation positions with different irradiation angles are referred to as "projection images". In a case in which the radiography system 1 performs the tomosynthesis imaging in which the radiation source 18 is moved to each of the irradiation positions $9t$ and the projection images are captured at each irradiation position $9t$, T projection images are obtained.

As illustrated in FIG. 2, the incident angle of the radiation R means an angle $\alpha$ formed between a line CL normal to the detection surface 22 of the radiation detector 20 and a radiation axis RC. Here, the detection surface 22 of the radiation detector 20 is substantially parallel to the imaging surface 14. Hereinafter, a predetermined range in which the incident angles are different from each other in the tomosynthesis imaging as illustrated in FIG. 2 is referred to as an "incident angle range". An example of the incident angle range is a range of ±10 degrees or ±20 degrees with respect to the line CL normal to the detection surface 22 of the radiation detector 20.

In contrast, in a case in which the radiography apparatus 10 performs the simple imaging, the radiation source 18 of the radiation emitting unit 16 is at an irradiation position (an irradiation position along a normal direction) where the irradiation angle $\alpha$ is 0 degrees. The radiation source 18 emits the radiation R in response to a command from the console 6 and the radiation detector 20 captures a radiographic image. Hereinafter, the radiographic image captured by the radiation detector 20 in the simple imaging is referred to as a "two-dimensional image".

In addition, as illustrated in FIG. 3, the radiography apparatus 10 according to this embodiment comprises the radiation detector 20, the radiation emitting unit 16, the radiation source driving unit 19, a control unit 30, a storage unit 32, an interface (I/F) unit 34, and an operation panel 36. The radiation detector 20, the radiation source 18, the control unit 30, the storage unit 32, the I/F unit 34, the operation panel 36, and the radiation source driving unit 19 are connected to each other through a bus 39 such as a system bus or a control bus.

The control unit 30 according to this embodiment comprises a central processing unit (CPU) 30A, a read only memory (ROM) 30B, and a random access memory (RAM) 30C. The CPU 30A controls the overall operation of the radiography apparatus 10 in response to a command from the console 6. For example, various programs including an image processing program (which will be described below) executed by the CPU 30A are stored in the ROM 30B in advance. The RAM 30C temporarily stores various kinds of data.

For example, the image data of the radiographic image captured by the radiation detector 20 and various other kinds of information are stored in the storage unit 32. Examples of the storage unit 32 include a hard disk drive (HDD) and a solid state drive (SSD). The I/F unit 34 transmits and receives various kinds of information to and from the console 6 using at least one of wireless communication or wired communication. For example, the operation panel 36 is provided as a plurality of switches in the imaging table 12 of the radiography apparatus 10. In addition, the operation panel 36 may be provided as a touch panel.

In contrast, the console 6 according to this embodiment controls the radiography apparatus 10, using, for example, an imaging order or various other kinds of information acquired from an external system, such as an RIS, through a wireless communication local area network (LAN). In addition, the console 6 according to this embodiment can generate a tomographic image which will be described in detail below, a slab image (which will be described in detail below), and a two-dimensional corresponding image (which will be described in detail below) from the projection images.

As illustrated in FIG. 3, the console 6 according to this embodiment comprises a control unit 40, a storage unit 42, an I/F unit 44, a display unit 46, and an operation unit 48. The control unit 40, the storage unit 42, the I/F unit 44, the display unit 46, and the operation unit 48 are connected to each other through a bus 49 such as a system bus or a control bus.

The control unit 40 according to this embodiment controls the overall operation of the console 6. The control unit 40 according to this embodiment comprises a CPU 40A, a ROM 40B, and a RAM 40C. The CPU 40A controls the overall operation of the console 6. For example, various programs including an image processing program (which will be described below) executed by the CPU 40A are stored in the ROM 40B in advance. The RAM 40C temporarily stores various kinds of data. The CPU 40A according to this embodiment executes the image processing program such that the control unit 40 functions as an example of an acquisition unit and a generation unit according to the present disclosure.

For example, the image data of the radiographic image captured by the radiography apparatus 10 and various other kinds of information are stored in the storage unit 42. Examples of the storage unit 42 include an HDD and an SSD.

The I/F unit 44 transmits and receives various kinds of information to and from the radiography apparatus 10 or external systems, such as an RIS and a picture archiving and communication system (PACS), using at least one of wireless communication or wired communication.

The display unit 46 displays, for example, information related to imaging and the captured radiographic images.

The operation unit 48 is used by a user to input, for example, a command to capture a radiographic image and a command related to image processing on the captured radiographic image. For example, the operation unit 48 may have the form of a keyboard or the form of a touch panel integrated with the display unit 46.

Next, the operation of the console 6 in the radiography system 1 according to this embodiment will be described. As described above, the console 6 according to this embodiment can generate a tomographic image and a slab image from a series of projection images captured by the tomosynthesis imaging. In addition, in this embodiment, the "tomographic image" is a radiographic image indicating the cross section (tomographic plane) of the subject W at a certain height in a height direction based on the detection surface 22 of the radiation detector 20. In addition, the "slab image" is a radiographic image having the information of the subject W in a certain range in the height direction. The console 6 according to this embodiment can generate, from a series of projection images, the same radiographic image as that captured by emitting the radiation R from the irradiation position (the irradiation position along the normal direction) where the irradiation angle α is 0 degrees. In this case, the radiographic image generated by the console 6 corresponds to a two-dimensional image captured in the simple imaging and is referred to as a "two-dimensional corresponding image". Hereinafter, in a case in which various radiographic images, such as a projection image, a two-dimensional image, a tomographic image, a slab image, and a two-dimensional corresponding image, are generically referred to without being distinguished from each other, they are simply referred to as "radiographic images".

First, a tomographic image generation method in the console 6 according to this embodiment will be described.

In the radiography system 1, in a case in which the tomosynthesis imaging that moves the radiation source 18 to each of the irradiation positions 9t and captures a projection image at each irradiation position 9t is performed, T projection images are obtained.

Figure 4:
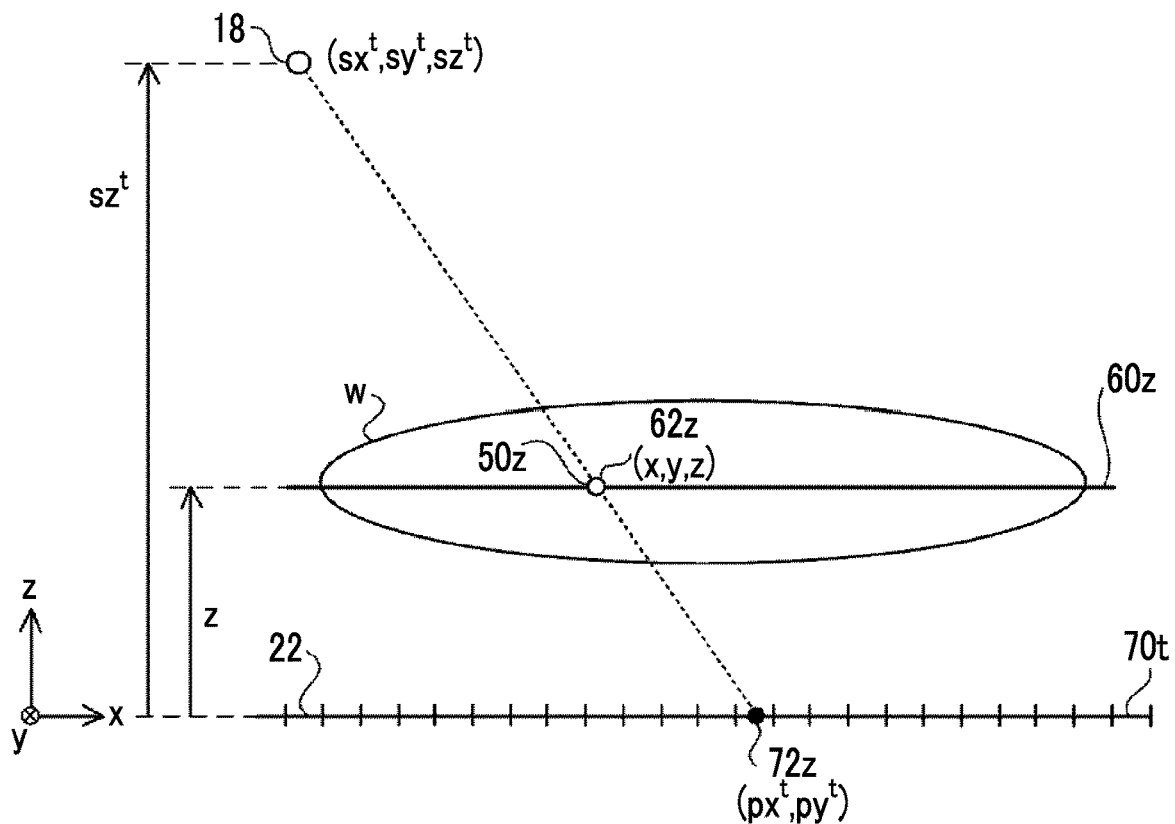
FIG. 4 is a diagram illustrating an example of a tomographic image generation method in the console according to the first embodiment.

As illustrated in FIG. 4, a main part 50z of the subject W which is at a height of z from the detection surface 22 of the radiation detector 20 (hereinafter, simply referred to as a "height") is projected to a position where a straight line connecting the radiation source 18 and the main part 50z intersects the detection surface 22. That is, a pixel 62z corresponding to the main part 50z in a tomographic image 60z that is located at a height of z (z>0) corresponds to a pixel 72z at a position where a straight line connecting the radiation source 18 and the pixel 62z intersects a projection image 70t. In addition, in this embodiment, the "position" of a pixel in the radiographic image means the coordinates indicating the position of the pixel in the radiographic image. The pixel 62z in this embodiment corresponds to an example of a pixel of interest according to the present disclosure.

A reconstruction processing method, such as a filter back projection (FBP) method or an iterative reconstruction method, adds the values pt(px$^t$, py$^t$) of each pixel 72z in a series of projection images 70t and divides the added value by the number T of the series of projection images 70t to derive a mean, thereby deriving the pixel value Rec(x, y, z) of the tomographic image 60z. Specifically, in a case in which the position of the radiation source 18 is (sx$^t$, sy$^t$, sz$^t$), the position of the pixel 62z is (x, y, z), and the position of the pixel 72z is (px$^t$, py$^t$), the pixel value Rec(x, y, z) of the tomographic image 60z is derived by the following Expression (1):

$$Rec(x, y, z) = \frac{1}{T}\sum_{t=1}^{T} P^t(px^t, py^t) = \tag{1}$$

$$\frac{1}{T}\sum_{t=1}^{T} P^t\left(\frac{sz^t}{sz^t - z} \times x - \frac{sz^t}{sz^t - z}sx^t, \frac{sz^t}{sz^t - z} \times y - \frac{sz^t}{sz^t - z}sy^t\right).$$

The console 6 derives the value of each pixel in the tomographic image 60z with the above-mentioned Expression (1) while changing the position (x, y) of the pixel to generate the entire tomographic image 60z at the height z.

Next, a slab image generation method in the console 6 according to this embodiment will be described. In this embodiment, for a method for generating a slab image with a slab thickness of 2d in the height range of z−d to z+d (0<d<z), two methods according to the following Examples 1 and 2 will be described. The height z−d in this embodiment is an example of a first height according to the present disclosure, the height z+d is an example of a second height according to the present disclosure, and the height z is an example of a third height according to the present disclosure.

EXAMPLE 1

Figure 5:
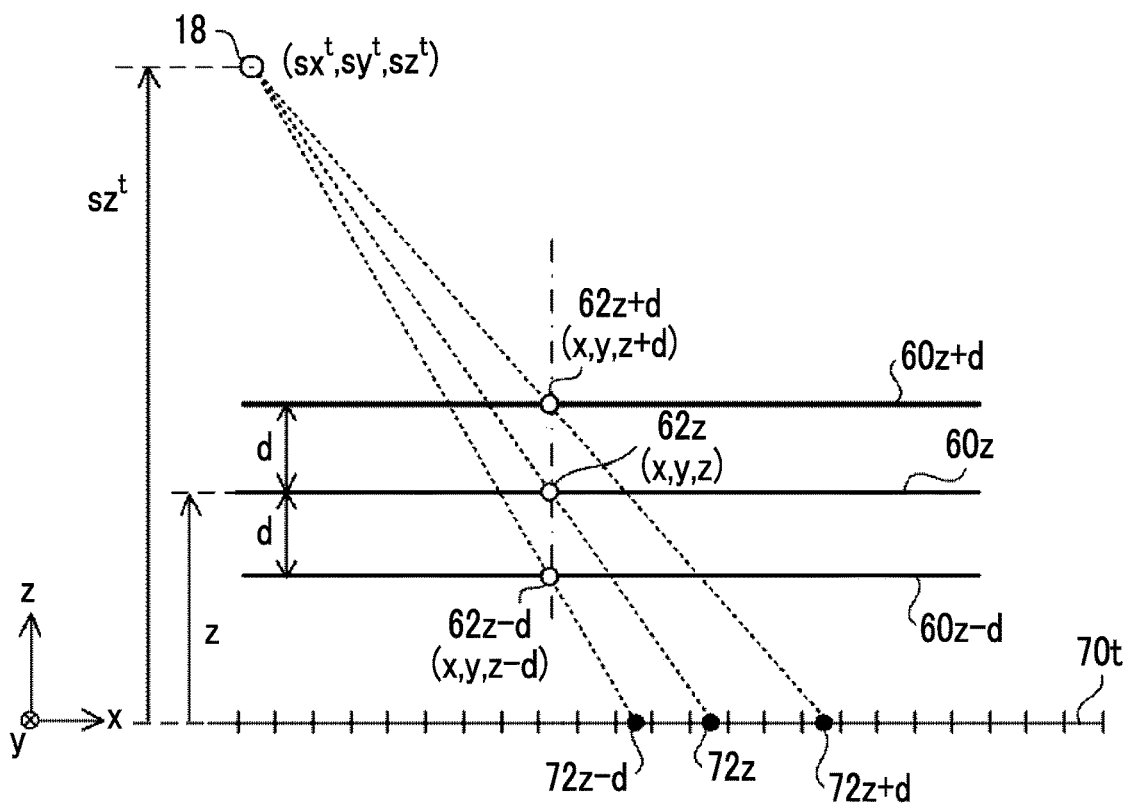
FIG. 5 is a diagram illustrating an example of a slab image generation method in the console according to the first embodiment.

First, a case in which a slab image is generated from three tomographic images, that is, a tomographic image 60z+d with a height of z+d, a tomographic image 60z with a height of z, and a tomographic image 60z−d with a height of z−d as illustrated in FIG. 5 will be described.

As illustrated in FIG. 5, a pixel 62z+d of the tomographic image 60z+d and a pixel 62z−d of the tomographic image 60z−d are located at the same position in the x direction and the y direction (the directions along the plane of the tomographic image 60z) as a pixel 62z of the tomographic image 60z and are different from the pixel 62z of the tomographic image 60z in height. In other words, the pixel 62z+d, the pixel 62z, and the pixel 62z−d have the same x-coordinate value and y-coordinate value. The pixel 62z+d corresponds to a pixel 72z+d at a position where a straight line connecting the radiation source 18 and the pixel 62z+d intersects the projection image 70t. Similarly, the pixel 62z−d corresponds to a pixel 72z−d at a position where a straight line connecting the radiation source 18 and the pixel 62z−d intersects the projection image 70t. In addition, the pixel 72z−d in this embodiment is an example of a first pixel in the present disclosure, the pixel 72z+d is an example of a second pixel in the present disclosure, and the pixel 72z is an example of the third pixel in the present disclosure.

The value Rec(x, y, z+d) of the pixel 62z+d is derived by the following Expression (2) and the value Rec(x, y, z−d) of the pixel 62z−d is derived by the following Expression (3) on the basis of the above-mentioned Expression (1).

$$Rec(x, y, z+d) = \frac{1}{T}\sum_{t=1}^{T} P^t\left(\frac{sz^t}{sz^t - (z+d)} \times x - \frac{sz^t}{sz^t - (z+d)}sx^t,\right. \tag{2}$$

$$\left.\frac{sz^t}{sz^t - (z+d)} \times y - \frac{sz^t}{sz^t - (z+d)}sy^t\right)$$

$$Rec(x, y, z-d) = \frac{1}{T}\sum_{t=1}^{T} P^t\left(\frac{sz^t}{sz^t - (z-d)} \times x - \frac{sz^t}{sz^t - (z-d)}sx^t,\right. \tag{3}$$

$$\left.\frac{sz^t}{sz^t - (z-d)} \times y - \frac{sz^t}{sz^t - (z-d)}sy^t\right).$$

Therefore, in the console 6 according to this embodiment, the slab image generated by the tomographic image 60z+d, the tomographic image 60z, and the tomographic image 60z−d is derived by the following Expression (4):

$$\text{Slab}(x,y,x)=\frac{1}{3}\times(\text{Rec}(x,y,z-d)+\text{Rec}(x,y,z)+\text{Rec}(x,y,z+d)) \quad (4).$$

The above-mentioned Expression (4) shows that the sum of the pixel values is divided by the number of tomographic images ("3" in this example) and the mean of the pixel values is used. However, the invention is not limited to the use of the mean of the pixel values. For example, any one of the maximum value, minimum value, and mode of the pixel values may be used. Alternatively, two or more of the mean, maximum value, minimum value, and mode of the pixel values may be combined and the combinations may be used according to, for example, the position of the pixel. In addition, a slab image may be generated using pixel values derived by applying a method, such as statistical analysis, to the pixel values of a tomographic image. An example of the statistical analysis in this case is regression analysis. A method which applies the regression analysis to pixel values to generate a slab image is disclosed in, for example, JP618503B. In addition, the number of tomographic images required to generate the slab image is not limited to "3" in this example.

EXAMPLE 2

Figure 6:
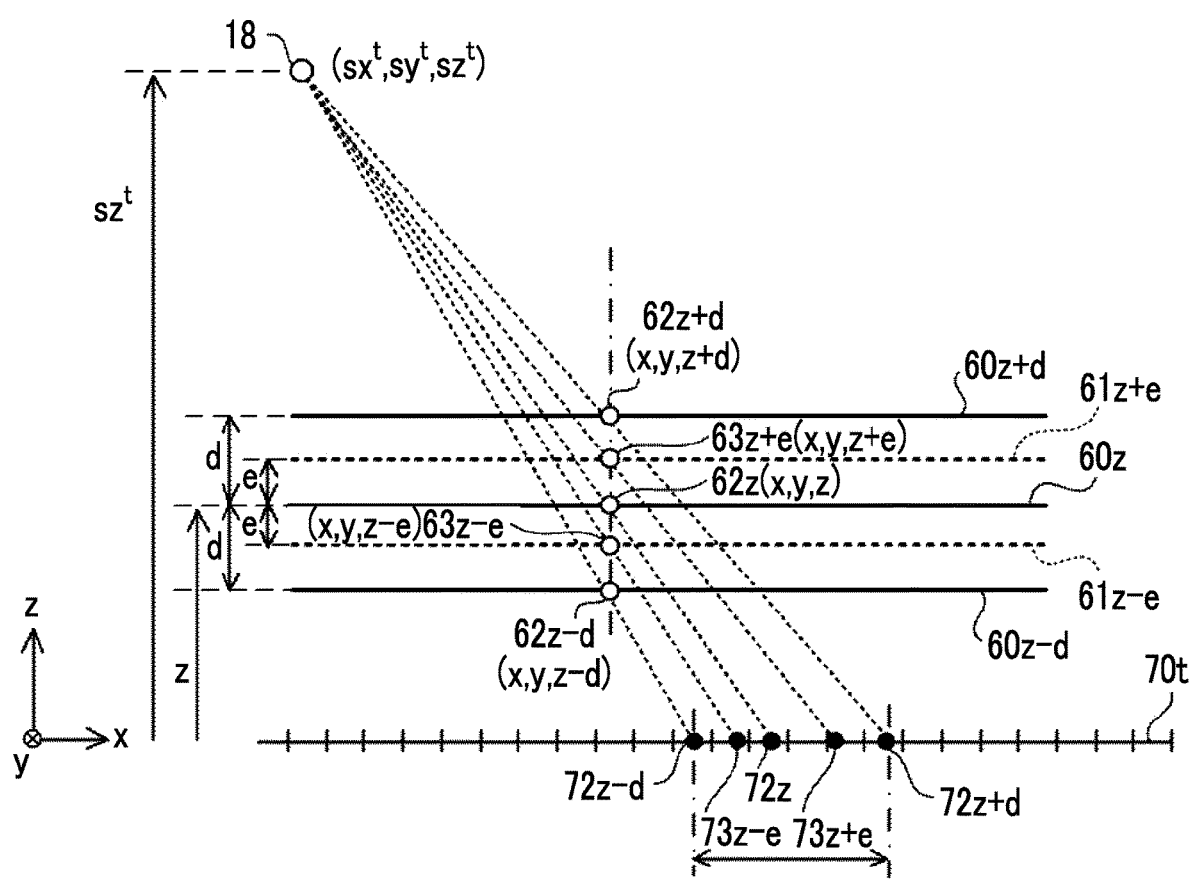
FIG. 6 is a diagram illustrating another example of the slab image generation method in the console according to the first embodiment.

The generation of a slab image which is equivalent to a case in which a slab image is generated from the tomographic images arranged at a narrower interval than that in Example 1 will be described with reference to FIG. 6. As illustrated in FIG. 6, a tomographic image 61z+e with a height of 60z+e (0<e<d) is present between the tomographic image 60z and the tomographic image 60z+d and a pixel 63z+e which is located at the same x-coordinate position and y-coordinate position as the pixels 62z−d, 62z, and 62z+d in the tomographic image 61z+e corresponds to a pixel 73z+e at a position where a straight line connecting the radiation source 18 and the pixel 63z+e intersects the projection image 70t. Therefore, the pixel 73z+e is located between the pixel 72z and the pixel 72z+d. In addition, a tomographic image 61z−e with a height of 60z−e is present between the tomographic image 60z and the tomographic image 60z−d and a pixel 63z−e which is located at the same x-coordinate position and y-coordinate position as the pixels 62z−d, 62z, and 62z+d in the tomographic image 61z−e corresponds to a pixel 73z−e at a position where a straight line connecting the radiation source 18 and the pixel 63z−e intersects the projection image 70t. Therefore, the pixel 73z−e is located between the pixel 72z−d and the pixel 72z.

As such, the pixels of the tomographic images between the tomographic image 60z−d and the tomographic image 60z+d are located between the pixel 72z−d and the pixel 72z+d (FIG. 6, see an interval L) of the projection image 70t. Therefore, the addition of the values of the pixels 72z−d to 72z+d is synonymous with the generation of a slab image from a plurality of tomographic images. For example, the addition of the values of the pixels in the interval L is synonymous with the generation of a slab image after the generation of the tomographic images most finely sliced in the depth direction (height direction) in principle.

Specifically, the values of the pixels included in the following range are used to generate a slab image:

$$\left(\frac{sz^t}{sz^t-(z-d)}\times x-\frac{sz^t}{sz^t-(z-d)}sx^t,\frac{sz^t}{sz^t-(z-d)}\times y-\frac{sz^t}{sz^t-(z-d)}sy^t\right)\sim$$
$$\left(\frac{sz^t}{sz^t-(z+d)}\times x-\frac{sz^t}{sz^t-(z+d)}sx^t,\right.$$
$$\left.\frac{sz^t}{sz^t-(z+d)}\times y-\frac{sz^t}{sz^t-(z+d)}sy^t\right).$$

The number of pixels (pixel numbers) included in the above-mentioned range varies depending on the projection image 70t. In a case in which the range of the pixels included in a t-th projection image 70t is represented by $(k_x, k_y) \in$ and the number of pixels included in the range is represented by Mt, a slab image with a thickness of ±d mm (2×d mm) is derived by the following Expression (5):

$$\text{Slab}(x,y,z) = \frac{1}{T}\sum_{t=1}^{T}\sum_{(k_x,k_y)\in R_t}\frac{p^t(k_x,k_y)}{M_t}. \quad (5)$$

The above-mentioned Expression (5) shows a case in which the pixel values are divided by the number of projection images 70t and the mean of the pixel values is used. However, the invention is not limited to the case in which the mean of the pixel values is used. Similarly to Example 1, for example, any one of the maximum value, minimum value, and mode of the pixel values may be used. Alternatively, two or more of the mean, maximum value, minimum value, and mode of the pixel values may be combined and the combinations may be used according to, for example, the position of the pixel. In addition, a slab image may be generated using pixel values derived by applying a method, such as statistical analysis, to the pixel values of a tomographic image.

Figure 7:
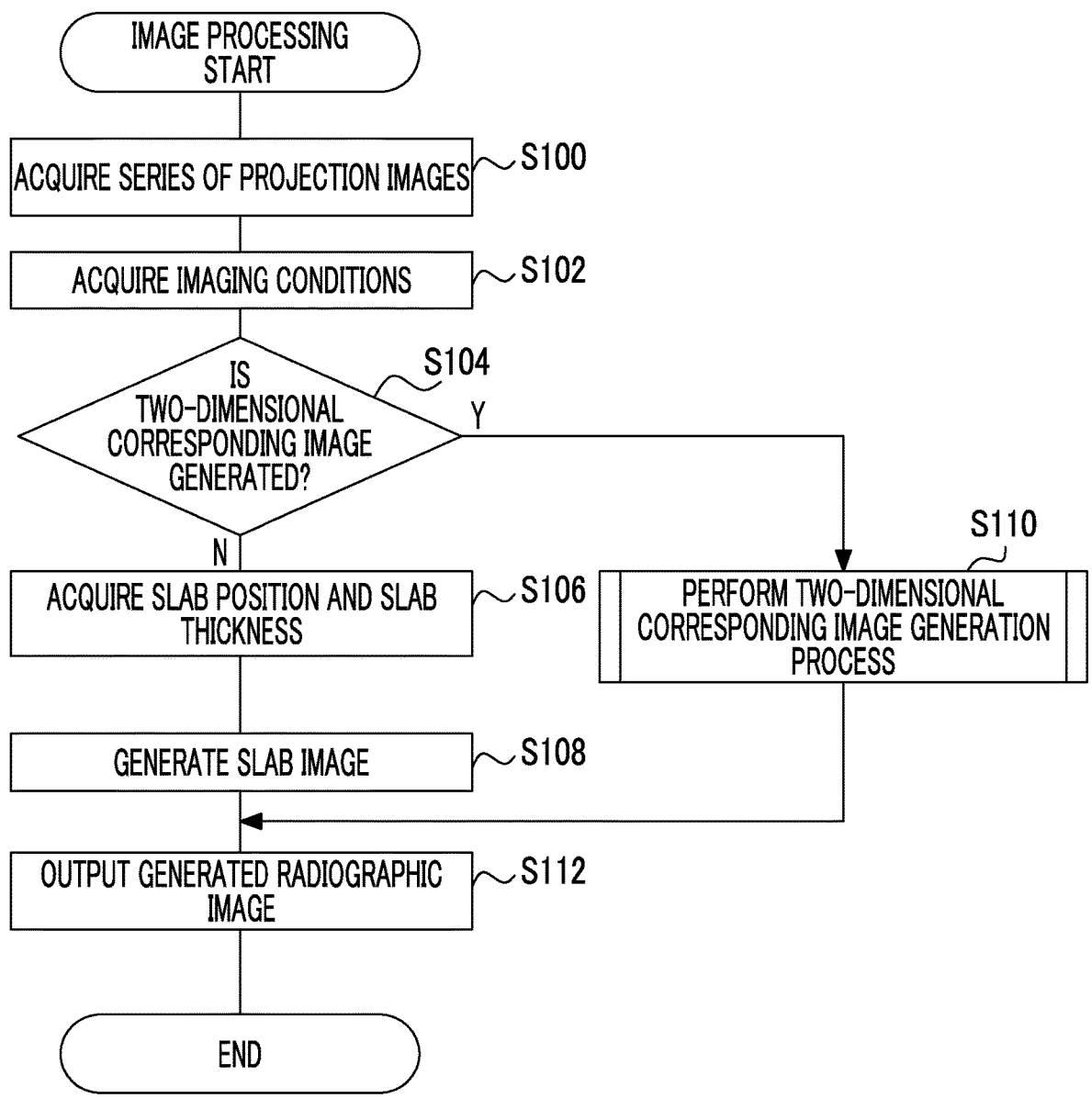
FIG. 7 is a flowchart illustrating an example of the flow of image processing performed by the console according to the first embodiment.

Next, the image processing operation of the console 6 according to this embodiment generating the slab image or the two-dimensional corresponding image will be described. FIG. 7 is a flowchart illustrating an example of the flow of the image processing performed by the control unit 40 of the console 6 according to this embodiment.

In the console 6 according to this embodiment, for example, in a case in which a command to display a slab image or a two-dimensional corresponding image is received from the user through the operation unit 48 of the console 6, the CPU 40A of the control unit 40 executes the image processing program stored in the ROM 40B to perform the image processing illustrated in FIG. 7.

As illustrated in FIG. 7, in Step S100, the control unit 40 acquires a series of projection images obtained by one tomosynthesis imaging operation. The acquisition destination of the projection image is not particularly limited as long as it is a device storing a desired projection image. For example, the acquisition destination may be the storage unit 42 of the host apparatus, the radiography apparatus 10, and a PACS.

Then, in Step S102, the control unit 40 acquires the imaging conditions of the acquired series of projection images. The imaging conditions acquired in this step are imaging conditions corresponding to parameters required to generate a slab image. In this embodiment, for example, the imaging conditions are the distance between the radiation source 18 and the detection surface 22 of the radiation detector 20 and the projection angle of each projection image. The control unit 40 acquires the imaging conditions from any position or acquires the imaging conditions using any method. For example, in a case in which the imaging conditions are also stored so as to be associated with the projection images acquired in Step S100, the control unit 40 may acquire both the projection images and the imaging conditions.

Then, in Step S104, the control unit 40 determines whether a command to display a two-dimensional corresponding image has been input. In a case in which the command to display a two-dimensional corresponding image has not been input, that is, in a case in which a command to display a slab image has been input, the determination result in Step S104 is "No" and the control unit 40 proceeds to Step S106.

In Step S106, the control unit 40 acquires the slab position and slab thickness of the slab image to be generated (displayed). A method for acquiring the slab position and the slab thickness in the control unit 40 is not particularly limited. For example, in a case in which the slab thickness is predetermined, the control unit 40 may divide the thickness of the subject W by the slab thickness to derive the number of slab images to be generated and derive the slab position according to the slab thickness and the number of slab images to derive the slab position and the slab thickness. In addition, for example, in a case in which the number of slab images to be generated is predetermined, the control unit 40 may derive, as the slab thickness, a value obtained by dividing the thickness of the subject W by the number of slab images and derive the slab position according to the number of slab images and the slab thickness to derive the slab position and the slab thickness.

For example, the control unit 40 may acquire the slab position and the slab thickness input from the user through the operation unit 48.

The number of slab images generated in this step is not particularly limited. For example, one slab image or a plurality of slab images may be generated.

Then, in Step S108, the control unit 40 generates a slab image. The control unit 40 generates a slab image from the series of projection images acquired in Step S100 on the basis of the imaging conditions acquired in Step S102 and the slab position and the slab thickness acquired in Step S106, using Expression (4) in Example 1 or Expression (5) in Example 2. Any of Expression (4) and Expression (5) may be used. For example, in a case in which Expression (4) is used, a processing load required for calculation is less than that in a case in which Expression (5) is used. In a case in which Expression (5) is used, accuracy tends to be higher than that in a case in which Expression (4) is used. Therefore, the expression to be used to generate the slab image may be determined on the basis of whether importance is attached to the processing load or accuracy.

On the other hand, in a case in which the command to display a two-dimensional corresponding image has been input, the determination result in Step S104 is "Yes" and the control unit 40 proceeds to Step S110.

Figure 8:
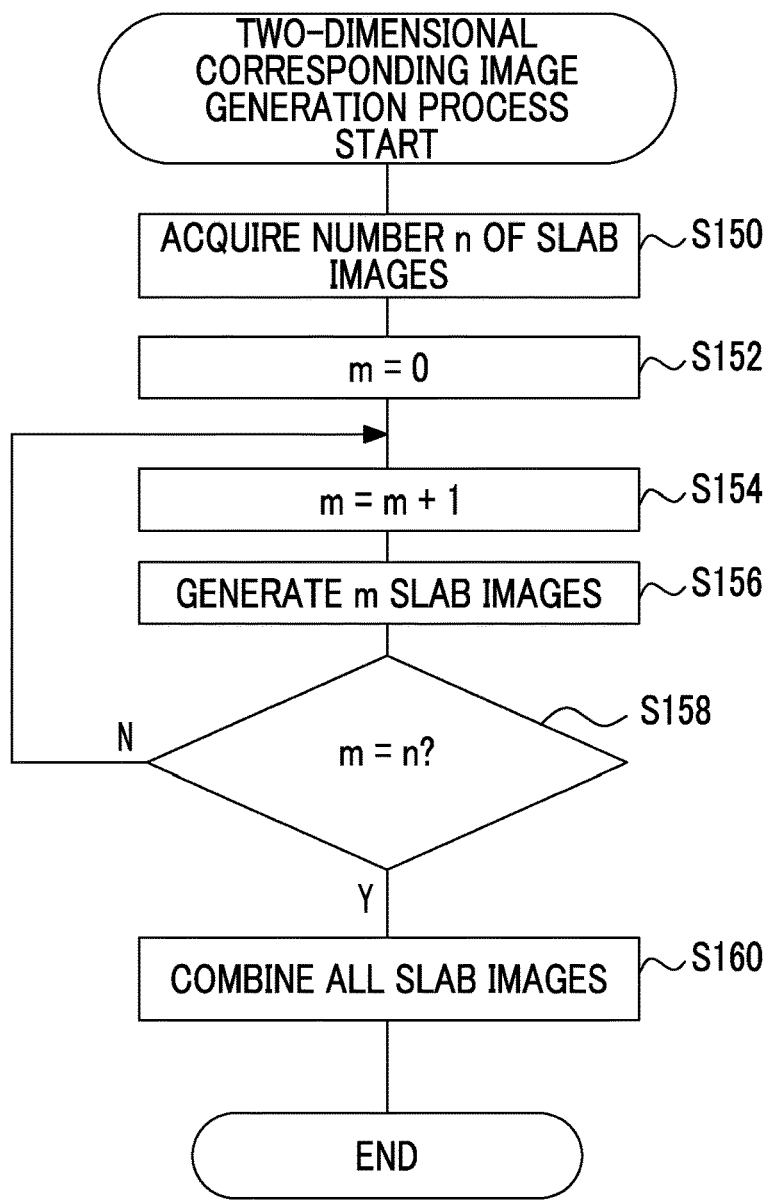
FIG. 8 is a flowchart illustrating an example of the flow of a two-dimensional corresponding image generation process in the image processing performed by the console according to the first embodiment.
Figure 9:
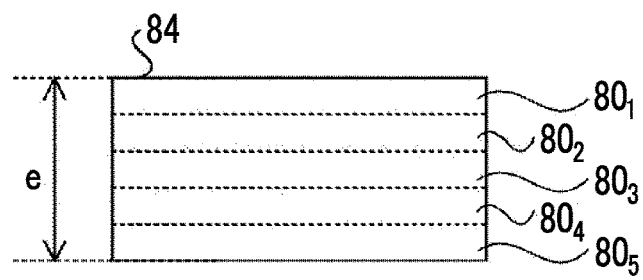
FIG. 9 is a diagram illustrating a method for generating a two-dimensional corresponding image using the two-dimensional corresponding image generation process illustrated in FIG. 8.

In Step S110, the control unit 40 performs a two-dimensional corresponding image generation process to generate a two-dimensional corresponding image from the series of projection images acquired in Step S100. FIG. 8 is a flowchart illustrating an example of the flow of the two-dimensional corresponding image generation process performed by the control unit 40 according to this embodiment. In the example of the two-dimensional corresponding image processing illustrated in FIG. 8, as illustrated in FIG. 9, a plurality of (five in FIG. 9) slab images 80 ($80_1$ to $80_5$) are generated and the plurality of generated slab images 80 are added to generate a two-dimensional corresponding image 84.

Therefore, in Step S150 illustrated in FIG. 8, the control unit 40 acquires the number n of slab images 80 generated. A method for acquiring the number n of slab images 80 in the control unit 40 is not particularly limited. For example, in a case in which the number of slab images 80 to be generated is predetermined, the control unit 40 may acquire a predetermined number n of slab images. In addition, for example, in a case in which the slab thickness of the slab image 80 to be generated is predetermined, the control unit 40 may acquire, as the number n of slab images generated, a value obtained by dividing the thickness (corresponding to a thickness e in FIG. 9) of the subject W by the slab thickness.

Then, in Step S152, the control unit 40 sets a variable m for managing the number of slab images 80 generated to "0" (m=0). Then, in Step S154, the control unit 40 adds "1" to the variable m. Then, in Step S156, the control unit 40 generates m slab images 80 from the series of projection images acquired in Step S100 according to the imaging conditions acquired in Step S102, using the above-mentioned Expression (4).

Then, in Step S158, the control unit 40 determines whether the variable m is equal to the number n acquired in Step S150 (m=n). In a case in which the variable m is not equal to the number n, that is, in a case in which there is a slab image 80 to be generated, the determination result in Step S158 is "No" and the control unit 40 proceeds to Step S154. Then, the process in Steps S154 and S156 is repeated. In other words, the process of changing the position of the slab image 80 to be generated in the thickness direction and generates the slab image 80 is repeated.

On the other hand, in a case in which the variable m is equal to the number n, that is, in a case in which all of the slab images 80 to be generated (five slab images 80 ($80_1$ to $80_5$) in the example illustrated in FIG. 9) have been generated, the determination result in Step S158 is "Yes" and the control unit 40 proceeds to Step S160.

In Step S160, the control unit 40 combines all of the slab images 80 generated in Step S156 to generate the two-dimensional corresponding image 84 and then ends the two-dimensional corresponding image generation process.

Figure 10:
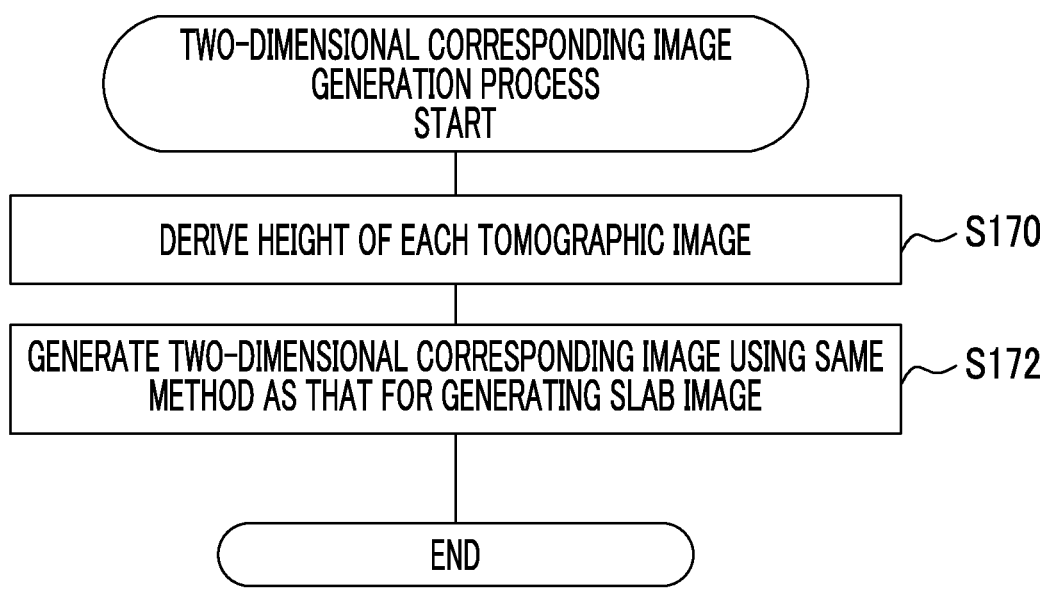
FIG. 10 is a flowchart illustrating another example of the two-dimensional corresponding image generation process in the image processing performed by the console according to the first embodiment.

The two-dimensional corresponding image generation process in Step S110 of the image processing, that is, the two-dimensional corresponding image generation method is not limited to the method illustrated in FIG. 8. For example, the two-dimensional corresponding image 84 to be generated may be regarded as one slab image 80 and the two-dimensional corresponding image 84 may be generated by the same method as one slab image 80. FIG. 10 is a flowchart illustrating an example of the flow of the two-dimensional corresponding image generation process performed by the control unit 40 according to this embodiment in this case.

In Step S170, the control unit 40 derives the height of each tomographic image required to generate the two-dimensional corresponding image 84 (slab image 80). As described above, in a case in which the slab image 80 is generated from three tomographic images 60 ($60z-d$, $60z$, and $60z+d$), the control unit 40 sets z and d to half the thickness of the subject W and derives, as the height of each tomographic image, three values, that is, 0, half the thickness of the subject W, and the thickness of the subject W.

Then, in Step S172, the control unit 40 generates a two-dimensional corresponding image from the series of projection images acquired in Step S100 according to the imaging conditions acquired in Step S102 using the above-mentioned Expression (4), similarly to the generation of the slab image, and then ends the two-dimensional corresponding image generation process.

In the image processing according to this embodiment, in a case in which the two-dimensional corresponding image generation process in Step S110 ends and in a case in which the process in Step S108 ends, the control unit 40 proceeds to Step S112.

In Step S112, the control unit 40 outputs the generated radiographic image (the slab image or the two-dimensional corresponding image) so as to be displayed on the display unit 46 and then ends the image processing.

As such, the control unit 40 of the console 6 according to this embodiment generates a slab image with a thickness corresponding to the range from the first height to the second height, using the values of the first pixels in a plurality of projection images corresponding to the coordinates of the pixel of interest in the tomographic plane whose height from the detection surface 22 of the radiation detector 20 is the first height and the values of the second pixels in a plurality of projection images corresponding to the coordinates of the pixel of interest in the tomographic plane at the second height different from the first height.

In addition, the control unit 40 of the console 6 according to this embodiment generates a two-dimensional corresponding image using the same method as the control unit 40 generates the slab image or combines the plurality of generated slab images to generate a two-dimensional corresponding image.

Therefore, according to the console 6 of this embodiment, it is possible to reduce an arithmetic processing load required to generate the slab image and the two-dimensional corresponding image.

Second Embodiment

Next, a second embodiment will be described in detail. In this embodiment, the same configurations and operations as those described in the first embodiment are denoted by the same reference numerals and the detailed description thereof will not be repeated.

Since the configurations of a radiography system 1, a console 6, and a radiography apparatus 10 are the same as those in the first embodiment, the description thereof will not be repeated. In this embodiment, image processing performed by the control unit 40 of the console 6 differs from the image processing (see FIG. 7) according to the first embodiment in some processes. Therefore, different processes will be described.

Figure 11:
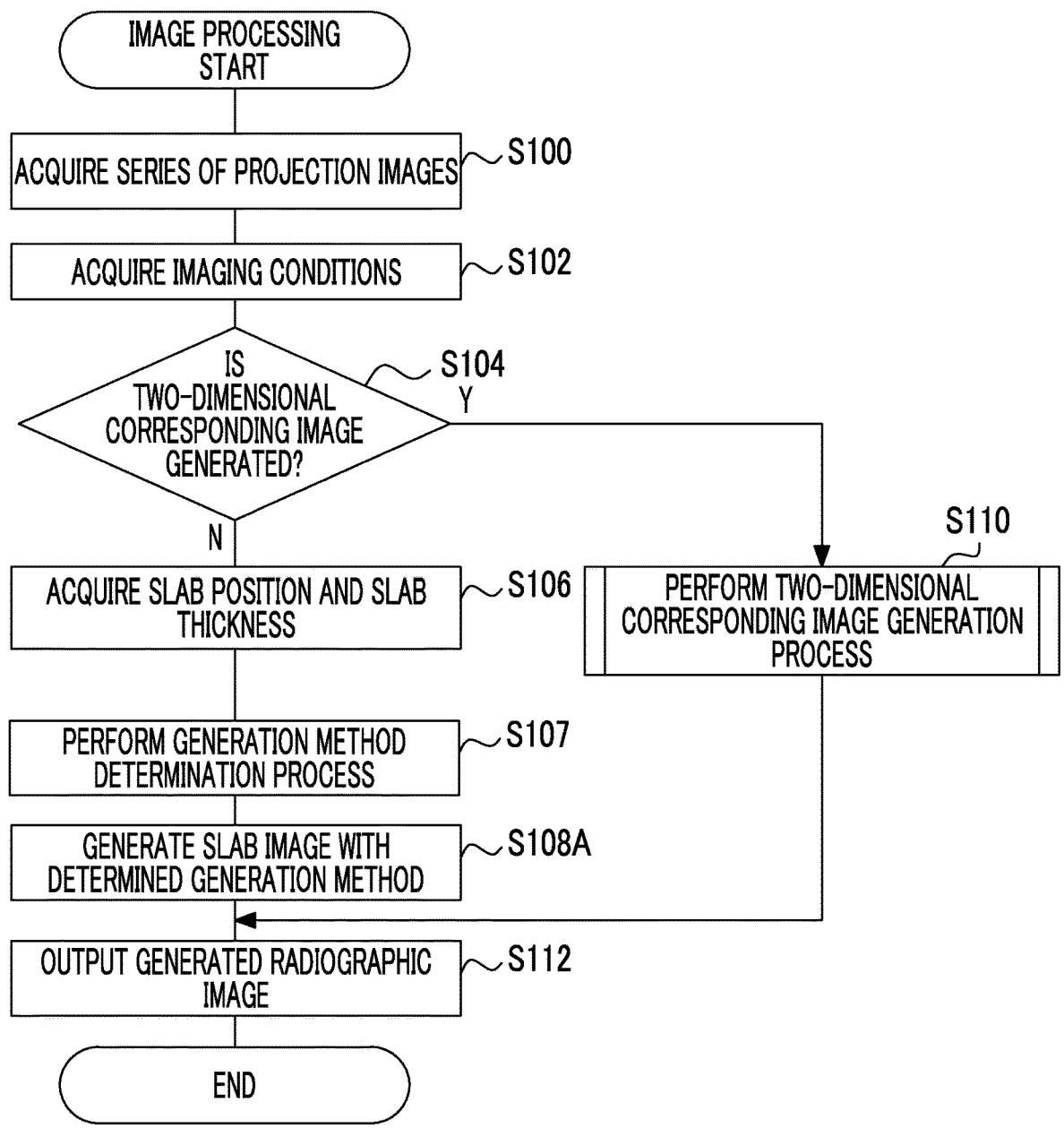
FIG. 11 is a flowchart illustrating an example of the flow of image processing performed by a console according to a second embodiment.

FIG. 11 is a flowchart illustrating an example of the flow of the image processing in the console 6 according to this embodiment. The image processing illustrated in FIG. 11 differs from the image processing (see FIG. 7) according to the first embodiment in that a process in Step S108A is performed instead of the process in Step S108 and a process in Step S107 is performed between Step S106 and Step S108A. Therefore, different processes will be described.

Figure 12:
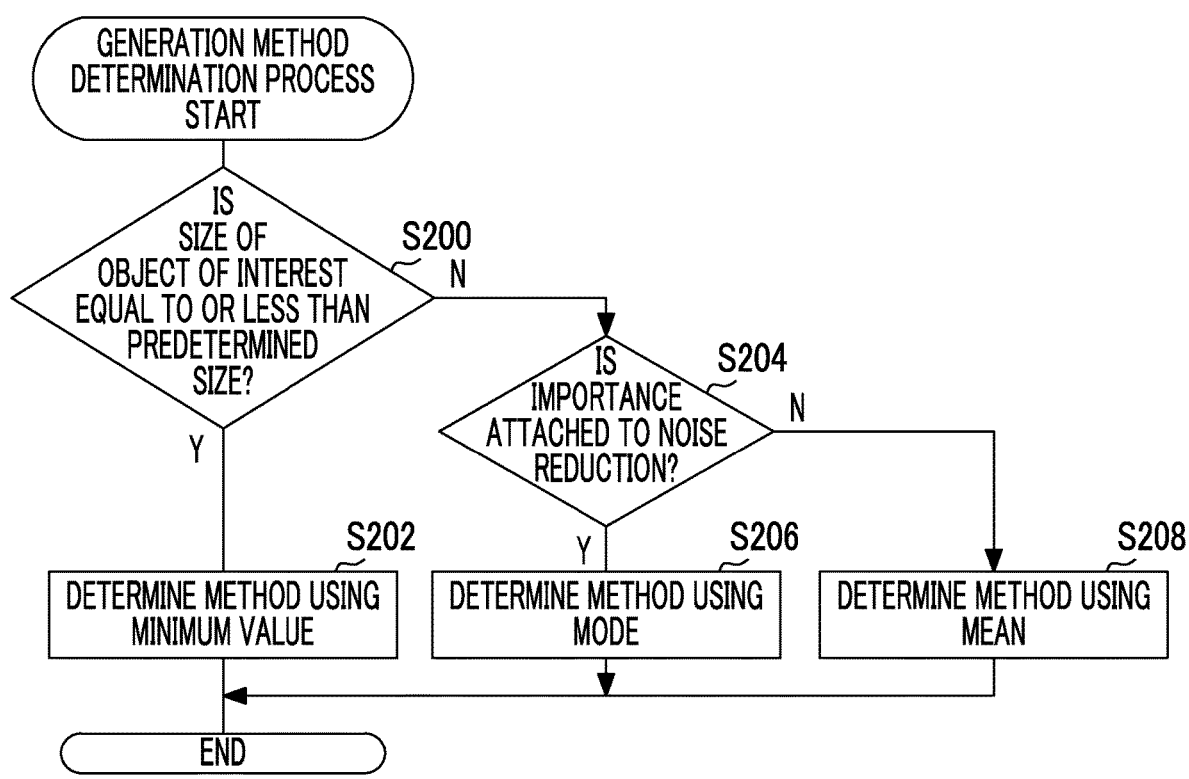
FIG. 12 is a flowchart illustrating an example of the flow of a generation method determination process in the image processing performed by the console according to the second embodiment.

In Step S107, the control unit 40 performs a generation method determination process to determine a slab image generation method from a plurality of generation methods. FIG. 12 is a flowchart illustrating an example of the flow of the generation method determination process performed by the control unit 40 according to this embodiment.

In Step S200, the control unit 40 determines whether the size of an object of interest is equal to or less than a predetermined size. In a case in which the object of interest to be observed by the user is a relatively small object of interest, such as calcification or a microstructure of bone, the pixel values of the image of the object of interest tend to be small. In this case, the minimum value of the pixel values is used in Expression (4) or Expression (5) described in the first embodiment. In this case, for example, the amount of blur of the slab image is less than that in a case in which the mean is used.

Therefore, in this embodiment, the threshold value of the size of the object of interest, at which the minimum value of the pixel values is preferably used, is predetermined and a slab image is generated using the minimum value of the pixel values in a case in which the size of the object of interest is equal to or less than the predetermined size.

Therefore, in a case in which the size of the object of interest is equal to or less than the predetermined size, the determination result in Step S200 is "Yes" and the control unit 40 proceeds to Step S202. A method for specifying the size of the object of interest is not particularly limited. For example, the size of the object of interest may be specified on the basis of information indicating the type of the object of interest such as calcification or a microstructure of bone.

In Step S202, the control unit 40 determines a method using the minimum value of the pixel values as the generation method in a case in which a slab image is generated by Expression (4) or Expression (5) described in the first embodiment in Step S108A that is the subsequent process and ends the generation method determination process.

On the other hand, in a case in which the size of the object of interest is not equal to or less than the predetermined size, that is, in a case in which the size of the object of interest is larger than the predetermined size, the determination result in Step S200 is "No" and the control unit 40 proceeds to Step S204.

In Step S204, the control unit 40 determines whether to attach importance to a reduction in the amount of noise in a slab image. In Expression (4) or Expression (5) described in the first embodiment, the mode of the pixel values is used to reduce the amount of noise in the slab image. In this embodiment, in a case in which importance is attached to a reduction in the amount of noise in a slab image, the mode of the pixel values is used to generate a slab image.

Therefore, in a case in which importance is attached to a reduction in the amount of noise in a slab image, the determination result in Step S204 is "Yes" and the control unit 40 proceeds to Step S206. A method for determining whether to attach importance to a reduction in the amount of noise in a slab image is not particularly limited. For example, whether to attach importance to a reduction in the amount of noise in a slab image may be determined on the basis of the type of the object of interest and the purpose of interpretation or may be determined on the basis of a command received from the user.

In Step S206, the control unit 40 determines a method using the mode of the pixel values as the generation method in a case in which a slab image is generated by Expression (4) or Expression (5) described in the first embodiment in Step S108A that is the subsequent process and ends the generation method determination process.

On the other hand, in a case in which importance is not attached to the reduction in the amount of noise in a slab image, the determination result in Step S204 is "No" and the control unit 40 proceeds to Step S208. In Step S208, the control unit 40 determines a method using the mean of the pixel values as the generation method in a case in which a slab image is generated by Expression (4) or Expression (5)

described in the first embodiment in Step S108A that is the subsequent process and ends the generation method determination process.

In the image processing according to this embodiment, in a case in which the generation method determination process in Step S107 ends in this way, the control unit 40 proceeds to Step S108A as illustrated in FIG. 11.

In Step S108A, a slab image is generated according to the generation method determined in Step S107, specifically, the determination of which of the minimum value, mode, and mean of the pixel values is used as described above, as in Step S108 of the image processing according to the first embodiment.

As such, the control unit 40 of the console 6 according to this embodiment determines which of the mean, minimum value, maximum value, and mode of the pixel value to use on the basis of the size of the object of interest in the subject W. Therefore, it is possible to prevent the deterioration of the image quality of a slab image.

Third Embodiment

Next, a third embodiment will be described in detail. In this embodiment, the same configurations and operations as those described in the first embodiment are denoted by the same reference numerals and the detailed description thereof will not be repeated.

Since the configurations of a radiography system 1, a console 6, and a radiography apparatus 10 are the same as those in the first embodiment, the description thereof will not be repeated. In this embodiment, image processing performed by the control unit 40 of the console 6 differs from the image processing (see FIG. 7) according to the first embodiment in some processes. Therefore, different processes will be described.

Figure 13:
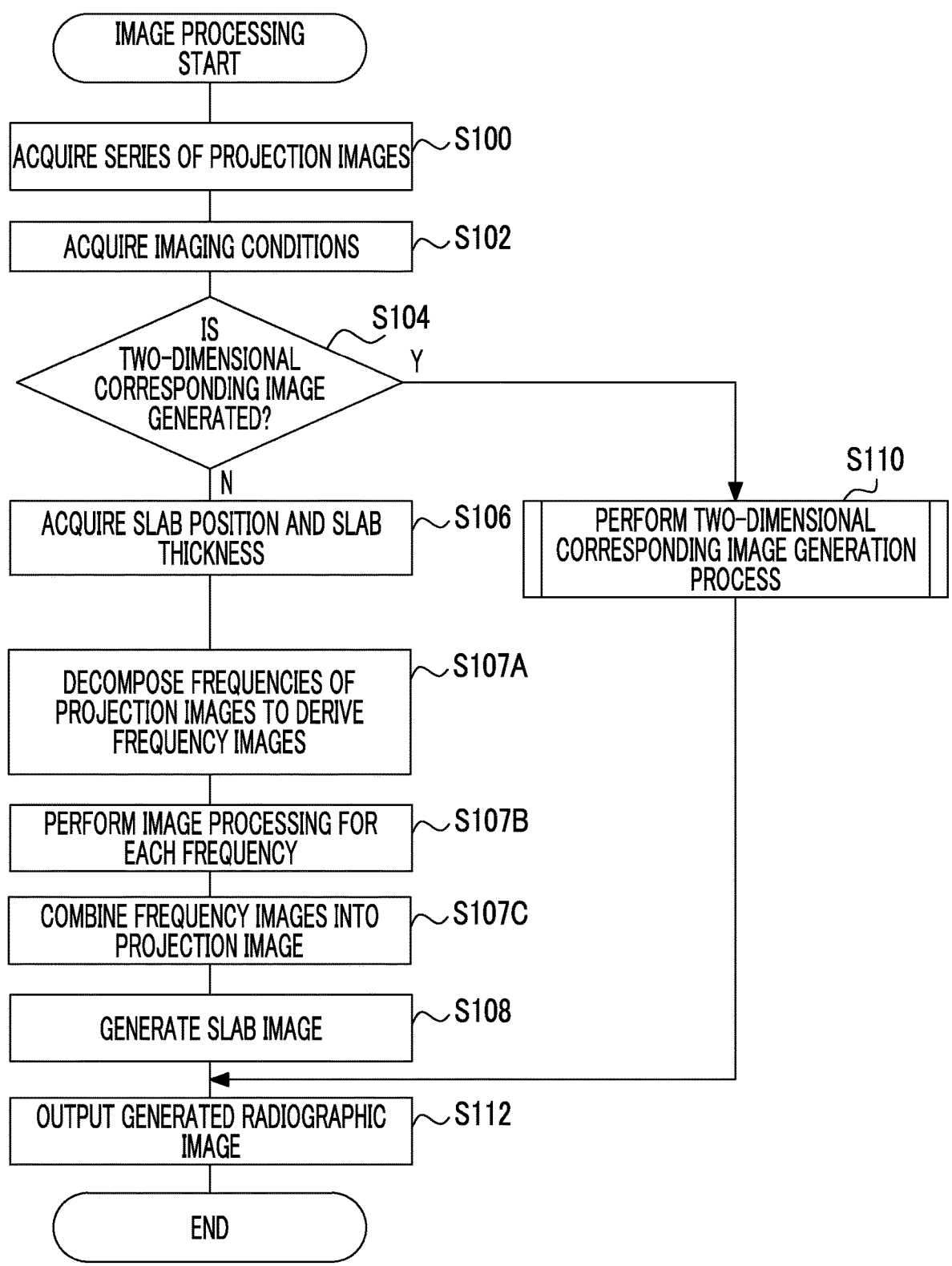
FIG. 13 is a flowchart illustrating an example of the flow of image processing performed by a console according to a third embodiment.

FIG. 13 is a flowchart illustrating an example of the flow of the image processing in the console 6 according to this embodiment. The image processing illustrated in FIG. 13 differs from the image processing (see FIG. 7) according to the first embodiment in that processes in Steps S107A to S107C are performed between Step S106 and Step S108. Therefore, different processes will be described.

In Step S107A, the control unit 40 decomposes the frequency of each of the series of projection images acquired in Step S100 to derive a plurality of frequency images indicating spatial frequencies in different bands.

A method for decomposing the frequency of the projection image in the control unit 40 is not particularly limited. Methods, such as Laplacian pyramid decomposition, wavelet transform, and unsharp mask, can be applied.

Then, in Step S107B, the control unit 40 performs predetermined image processing for each frequency of the frequency images derived in Step S107A. The image processing performed in this step is not particularly limited. An example of the image processing is filter processing using a frequency filter (for example, a low-pass filter) corresponding to the frequency.

Then, in Step S107C, the control unit 40 combines the frequency images processed in Step S107B into a projection image.

As such, the control unit 40 of the console 6 according to this embodiment decomposes each of a plurality of projection images into a plurality of frequency images indicating spatial frequencies in different bands, performs different types of image processing for the plurality of frequency images, combines the plurality of frequency images into a projection image, and generates a slab image on the basis of the combined projection images. Therefore, according to the console 6 of this embodiment, it is possible to further improve the quality of a slab image.

As described above, in the console 6 according to each of the above-described embodiments, the control unit 40 functions as an acquisition unit and a generation unit according to the present disclosure. The acquisition unit acquires a plurality of projection images obtained by irradiating the subject W disposed between the radiation source 18 and the radiation detector 20 with the radiation R emitted from the radiation source 18 at different irradiation angles and capturing the radiation with the radiation detector 20 at each of the irradiation angles. The generation unit generates a slab image with a thickness corresponding to the range from the first height to the second height, using the value of the first pixel in each of the plurality of projection images corresponding to the coordinates of the pixel of interest in the tomographic plane whose height from the detection surface 22 of the radiation detector 20 is the first height and the value of the second pixel in each of the plurality of projection images corresponding to the coordinates of the pixel of interest in the tomographic plane at the second height different from the first height.

Therefore, according to the console 6 of each of the above-described embodiments, it is possible to reduce an arithmetic processing load required to generate a slab image. In particular, according to the console 6 of each of the above-described embodiments, even in a case in which a slab image is generated using the same number of tomographic images, an arithmetic processing load required to generate the slab image can be less than that in the techniques according to the related art disclosed in WO2016/099924A and JP2015-159961A.

Therefore, according to the console 6 of each of the above-described embodiments, it is possible to reduce the time required to generate the slab image. In addition, according to the console 6 of each of the above-described embodiments, it is possible to reduce, for example, memory capacity required for arithmetic processing.

In each of the above-described embodiments, various processors other than the CPU may perform the image processing performed by the execution of software (program) by the CPU. In this case, examples of the processor include a programmable logic device (PLD) whose circuit configuration can be changed after manufacture, such as a field-programmable gate array (FPGA), and a dedicated electric circuit, such as an application specific integrated circuit (ASIC), which is a processor having a dedicated circuit configuration designed to perform a specific process. In addition, the image processing may be performed by one of the various processors or may be performed by a combination of two or more processors of the same type or different types (for example, a combination of a plurality of FPGAs and a combination of a CPU and an FPGA). Specifically, the hardware structure of the various processors is an electric circuit obtained by combining circuit elements such as semiconductor elements.

In each of the above-described embodiments, the aspect in which various programs stored in the control unit 30 of the radiography apparatus 10 and the control unit 40 of the console 6 are stored (installed) in the ROMs (30B and 40B) of the control unit 30 and the control unit 40 in advance has been described. However, the invention is not limited thereto. The image processing program may be recorded on a recording medium, such as a compact disk read only memory (CD-ROM), a digital versatile disk read only memory (DVD-ROM), or a universal serial bus (USB)

memory, and then provided. In addition, the image processing program may be downloaded from an external apparatus through the network.

In each of the above-described embodiments, the radiation R is not particularly limited. For example, X-rays or γ-rays may be applied.

In addition, for example, the configurations and operations of the radiography system 1, the console 6, and the radiography apparatus 10 according to each of the above-described embodiments are illustrative and may be changed according to the situation, without departing from the scope and spirit of the invention. In addition, the above-described embodiments may be appropriately combined with each other.

EXPLANATION OF REFERENCES

1: radiography system
6: console
9*t*: irradiation position
10: radiography apparatus
12: imaging table
14: imaging surface
16: radiation emitting unit
18: radiation source
19: radiation source driving unit
20: radiation detector
22: detection surface
30, 40: control unit
30A, 40A: CPU
30B, 40B: ROM
30C, 40C: RAM
32, 42: storage unit
34, 44: I/F unit
36: operation panel
39, 49: bus
46: display unit
48: operation unit
50*z*: main part
60*z*−*d*, 60*z*, 60*z*+*d*, 61*z*−*e*, 61*z*+*e*: tomographic image
62*z*−*d*, 62*z*, 62*z*+*d*, 63*z*−*e*, 63*z*+*e*, 72*z*−*d*, 72*z*, 72*z*+*d*, 73*z*−*e*, 73*z*+*e*: pixel
70*t*: projection image
80, 80$_1$ to 80$_5$: slab image
84: two-dimensional corresponding image
CL: normal line
R: radiation
RC: radiation axis
W: subject
α, θ: angle

What is claimed is:

1. An image processing apparatus comprising:
a processor configured to:
acquire a plurality of projection images obtained by irradiating a subject disposed between a radiation source and a radiation detector with radiation emitted from the radiation source at different irradiation angles and capturing the radiation with the radiation detector at each of the irradiation angles; and
generate a slab image with a thickness corresponding to a range from a first height to a second height different from the first height, using a value of a first pixel in each of the plurality of projection images corresponding to coordinates of a pixel of interest in a tomographic plane whose height from a detection surface of the radiation detector is the first height and a value of a second pixel in each of the plurality of projection images corresponding to the coordinates of the pixel of interest in a tomographic plane at the second height.

2. The image processing apparatus according to claim 1, wherein the processor generates the slab image further using a value of a third pixel in each of the plurality of projection images corresponding to the coordinates of the pixel of interest in a tomographic plane at a third height of at least a position between the first height and the second height.

3. The image processing apparatus according to claim 2, wherein the processor generates the slab image using at least one of a mean, a minimum value, a maximum value, or a mode of the value of the first pixel in each of the plurality of projection images, the value of the second pixel in each of the plurality of projection images, and the value of the third pixel in each of the plurality of projection images.

4. The image processing apparatus according to claim 3, wherein the processor determines which of the mean, the minimum value, the maximum value, and the mode to use, on the basis of a size of an object of interest in the subject.

5. The image processing apparatus according to claim 2, wherein the first height is a height of a lowermost portion in the height direction and the second height is a height of an uppermost portion in the height direction.

6. The image processing apparatus according to claim 2, wherein the processor generates a plurality of the slab images while changing the first height and the second height in the height direction and combines the plurality of generated slab images to further generate a two-dimensional corresponding image.

7. The image processing apparatus according to claim 2, wherein the processor decomposes each of the plurality of projection images into a plurality of frequency images indicating spatial frequencies in different bands, performs different types of image processing for the plurality of frequency images, combines the plurality of frequency images to generate a plurality of projection images, and generates the slab image on the basis of the plurality of combined projection images.

8. The image processing apparatus according to claim 3, wherein the first height is a height of a lowermost portion in the height direction and the second height is a height of an uppermost portion in the height direction.

9. The image processing apparatus according to claim 3, wherein the processor generates a plurality of the slab images while changing the first height and the second height in the height direction and combines the plurality of generated slab images to further generate a two-dimensional corresponding image.

10. The image processing apparatus according to claim 3, wherein the processor decomposes each of the plurality of projection images into a plurality of frequency images indicating spatial frequencies in different bands, performs different types of image processing for the plurality of frequency images, combines the plurality of frequency images to generate a plurality of projection images, and generates the slab image on the basis of the plurality of combined projection images.

11. The image processing apparatus according to claim 1, wherein the processor generates the slab image using values of pixels located from the first pixel to the second pixel in each of the plurality of projection images.

12. The image processing apparatus according to claim 11,
wherein the processor generates the slab image using at least one of a mean, a minimum value, a maximum value, or a mode of the values of the pixels located from the first pixel to the second pixel in each of the plurality of projection images.

13. The image processing apparatus according to claim 12,
wherein the processor determines which of the mean, the minimum value, the maximum value, and the mode to use, on the basis of a size of an object of interest in the subject.

14. The image processing apparatus according to claim 11,
wherein the first height is a height of a lowermost portion in the height direction and the second height is a height of an uppermost portion in the height direction.

15. The image processing apparatus according to claim 11,
wherein the processor generates a plurality of the slab images while changing the first height and the second height in the height direction and combines the plurality of generated slab images to further generate a two-dimensional corresponding image.

16. The image processing apparatus according to claim 1,
wherein the first height is a height of a lowermost portion in the height direction and the second height is a height of an uppermost portion in the height direction.

17. The image processing apparatus according to claim 1,
wherein the processor generates a plurality of the slab images while changing the first height and the second height in the height direction and combines the plurality of generated slab images to further generate a two-dimensional corresponding image.

18. The image processing apparatus according to claim 1,
wherein the processor decomposes each of the plurality of projection images into a plurality of frequency images indicating spatial frequencies in different bands, performs different types of image processing for the plurality of frequency images, combines the plurality of frequency images to generate a plurality of projection images, and generates the slab image on the basis of the plurality of combined projection images.

19. An image processing method using the image processing apparatus according to claim 1 comprising:
acquiring the plurality of projection images obtained by irradiating the subject disposed between a radiation source and a radiation detector with radiation emitted from the radiation source at different irradiation angles and capturing the radiation with the radiation detector at each of the irradiation angles; and
generating the slab image with the thickness corresponding to the range from the first height to the second height different from the first height, using the value of the first pixel in each of the plurality of projection images corresponding to coordinates of the pixel of interest in the tomographic plane whose height from the detection surface of the radiation detector is the first height and the value of the second pixel in each of the plurality of projection images corresponding to the coordinates of the pixel of interest in the tomographic plane at the second height.

20. A non-transitory recording medium storing an image processing program that causes a computer to perform:
acquiring a plurality of projection images obtained by irradiating a subject disposed between a radiation source and a radiation detector with radiation emitted from the radiation source at different irradiation angles and capturing the radiation with the radiation detector at each of the irradiation angles; and
generating a slab image with a thickness corresponding to a range from a first height to a second height different from the first height, using a value of a first pixel in each of the plurality of projection images corresponding to coordinates of a pixel of interest in a tomographic plane whose height from a detection surface of the radiation detector is the first height and a value of a second pixel in each of the plurality of projection images corresponding to the coordinates of the pixel of interest in a tomographic plane at the second height.

* * * * *